(12) United States Patent
Ross et al.

(10) Patent No.: US 6,945,964 B2
(45) Date of Patent: Sep. 20, 2005

(54) HYPODERMIC NEEDLE

(76) Inventors: Chauncey F. Ross, deceased, late of Cortland, OH (US); by Dianne L. Hilderbrand, legal representative, 241 Golf Dr., Cortland, OH (US) 44410-1179

( * ) Notice: Subject to any disclaimer, the term of this patent is extended or adjusted under 35 U.S.C. 154(b) by 30 days.

(21) Appl. No.: 10/685,310

(22) Filed: Oct. 14, 2003

(65) Prior Publication Data

US 2004/0087915 A1 May 6, 2004

Related U.S. Application Data

(62) Division of application No. 10/286,707, filed on Oct. 31, 2002, now Pat. No. 6,702,790.

(51) Int. Cl.$^7$ .............................. A61M 5/32; A61M 5/00
(52) U.S. Cl. ....................................... 604/272; 604/239
(58) Field of Search ................................ 604/272, 274, 604/264, 239; 606/185, 186; 600/576

(56) References Cited

U.S. PATENT DOCUMENTS

| | | | | |
|---|---|---|---|---|
| 2,699,784 A | * | 1/1955 | Krayl | 606/185 |
| 3,119,391 A | * | 1/1964 | Harrison | 604/272 |
| 3,905,371 A | * | 9/1975 | Stickl et al. | 604/46 |
| 3,906,932 A | * | 9/1975 | Ayres | 600/577 |
| 4,490,139 A | * | 12/1984 | Huizenga et al. | 604/57 |
| 4,585,446 A | * | 4/1986 | Kempf | 604/274 |
| 4,666,438 A | * | 5/1987 | Raulerson | 604/272 |
| 4,753,641 A | * | 6/1988 | Vaslow | 604/274 |
| 5,064,411 A | * | 11/1991 | Gordon, III | 604/48 |
| 5,254,106 A | * | 10/1993 | Feaster | 604/272 |
| 5,632,728 A | * | 5/1997 | Hein | 604/46 |
| 5,669,890 A | * | 9/1997 | Grimm | 604/272 |
| 5,752,942 A | * | 5/1998 | Doyle et al. | 604/274 |
| 5,931,794 A | * | 8/1999 | Pitesky | 600/556 |
| 5,938,635 A | * | 8/1999 | Kuhle | 604/506 |
| 5,968,022 A | * | 10/1999 | Saito | 604/272 |
| 6,007,555 A | * | 12/1999 | Devine | 606/169 |
| 6,224,618 B1 | * | 5/2001 | Gordon | 606/185 |
| D476,419 S | * | 6/2003 | Swenson | D24/130 |
| 6,702,790 B1 | * | 3/2004 | Ross et al. | 604/272 |
| 6,726,649 B2 | * | 4/2004 | Swenson et al. | 604/46 |

* cited by examiner

Primary Examiner—Sharon Kennedy
(74) Attorney, Agent, or Firm—Armstrong, Kratz, Quintos, Hanson & Brooks, LLP

(57) ABSTRACT

A medical needle adapted for conducting fluid comprising a generally cylindrical tube having a central longitudinal axis, a first end and a second pointed end adapted for penetration into a bodily cavity of a subject, wherein the pointed end includes a plurality of prongs defined by at least one notch formed in the pointed end. Said notch between the prongs being beveled to allow for easy penetration of the needle into a blood-vessel.

5 Claims, 6 Drawing Sheets

HYPODERMIC NEEDLE

RELATED APPLICATIONS

This application is a division of Ser. No. 10/286,707, filed Oct. 31, 2002, and now U.S. Pat. No. 6,702,790.

FIELD OF THE INVENTION

The present invention relates generally to surgical products and, more particularly, to medical needles for penetrating bodily cavities, including fluid conducting needles and the like.

BACKGROUND OF THE INVENTION

Intravenous (I. V.) Needles, catheters and the like are known in the medical arts as the means by which fluids are introduced into and withdrawn from a fluid-carrying body cavity such as, for example, a blood vessel including a vein or an artery. The typical I. V. needle consists of an elongated, generally cylindrical tube formed of surgical steel having one end which is ground, cut or otherwise formed to provide a pointed, gently sloping portion adapted for penetration through the subject's skin and into a selected body cavity, e.g., a blood vessel. Once properly situated within the body cavity, fluids including, but not limited to, blood, blood products, nutrients and drugs, may be infused into and/or: extracted from the body cavity through the I. V. needle.

In perhaps the most common use of I. V. needles, an I. V. needle or catheter is inserted into a blood vessel. Medical personnel experienced in inserting such needles can, for many patients, properly insert the needle into a selected vein or artery in one or two attempts so as to achieve satisfactory fluid flow through the needle. However, for many other patients whose vasculature may not be readily accessible for reasons including, inter alia, displacement of the yieldable vessel resulting from contact by the inserted needle, small vessel size, excessive depth of the vessel beneath the skin, and the like, several insertions of the needle may be required before sufficient penetration of the vessel is accomplished and acceptable fluid flow through the needle can be established. As a consequence, these latter patients must endure the pain and trauma of being repeatedly pierced by sharp and sometimes relatively large diameter needles before sufficient fluid flow is attained. Further, in instances of emergency in which medical fluids must be quickly introduced into the patient, excessive time spent attempting to properly insert and place the needle may result in potentially harmful delay in administration of necessary emergency treatment with possible, dire consequences for the patient.

An advantage exists, therefore, for a medical needle which can reliably penetrate a body cavity, particularly a blood vessel, whereby satisfactory fluid flow into or from the body cavity through the needle can generally be achieved by a single insertion of the needle into a patient.

Prior Art Patents

Gordon (U.S. Pat. No. 5,064,411) shows a hypodermic needle with a serrated or pronged tip. However, the Gordon needle is distinct from the needle of the instant invention in that the area between the prongs is different in a material way. In the Gordon needle the area between the prongs is blunt so that the prongs and the blunt portion can be caught by fabric and thereby prevent the needle from inadvertently puncturing the skin as best shown in FIG. 3 of Gordon. On the other hand, the area between the prongs of applicant's device is beveled so as to create a cutting edge to facilitate entry of the needle into the vein. This is best shown in FIGS. 6A–6D.

BRIEF SUMMARY OF THE INVENTION

The present invention provides an intravenous medical needle having a configuration specifically adapted to enable the needle to reliably penetrate a body cavity including a blood vessel such as a vein or an artery, such that satisfactory fluid flow into or from the blood vessel through the needle can generally be achieved by a single insertion of the needle into a patient, notwithstanding the condition of the patient's vasculature. The needle of this invention comprises an elongated, generally cylindrical tube preferably formed of surgical steel or other suitable material having one end which is ground, cut or otherwise formed so as to provide a pointed, gently sloping end adapted for penetration through a subject's skin and into the selected body cavity, e.g., a blood vessel. The pointed end of the needle includes a plurality of prongs or tines defined by at least one notch formed between the prongs or tines for enhancing the likelihood of engagement and penetration of the wall of the selected body cavity upon insertion of the needle through a patient's skin.

The herein disclosed invention envisions a medical needle adapted for conducting fluid, said needle comprising: a generally cylindrical tube having a central longitudinal axis, a first end and a second pointed end adapted for penetration into a body cavity of a subject; and a plurality of prongs provided in said pointed end, wherein between said plurality of prongs there is a notch having a beveled edge for facilitating the entry of the pointed end of the needle into a body cavity. Said medical needle can have two prongs or three prongs or more. The pointed end of the medical needle can slope at a first angle relative to said central axis and said at least one notch slopes at a second angle relative to said first angle. In the needle with two prongs, the prongs are spaced apart substantially less than 180 degrees along the circumference.

Other details, objects and advantages of the present invention will become apparent as the following description of the presently preferred embodiments and presently preferred methods of practicing the invention proceeds.

BRIEF DESCRIPTION OF THE DRAWINGS

FIGS. 5A–6D are views comparing the prior art double-tipped hypodermic needle 30 with the double-tipped hypodermic needle of the herein disclosed invention 20. FIGS. 5A and 6A are comparative perspective views of the needle tips. FIGS. 5A–5D show tips 32 as disclosed in the double tipped needle 30 of the Gordon patent (U.S. Pat. No. 5,064,441) while FIGS. 6A–6D describe the double tips 22 of the needle 20 of the invention. Note particularly that in the prior art the needle points 32 (FIGS. 5A–5D) the area 34 between the prongs 32 is blunt 34 while FIGS. 6A–6D the area 24 between the prongs 22 is beveled (or sharp) 24.

The invention will become more readily apparent from the following description of preferred embodiments thereof shown, by way of example only.

DESCRIPTION OF THE INVENTION

Figure 1A:
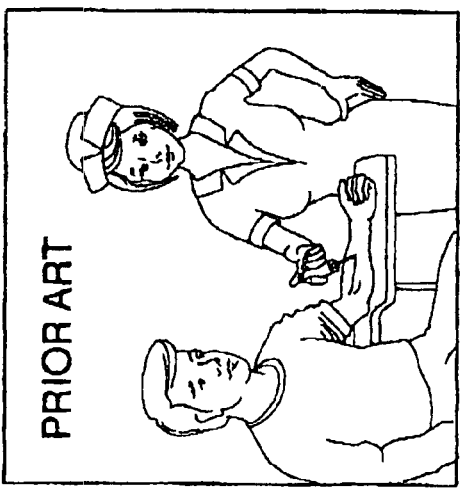
FIGS. 1A–2C are pictorial views describing the shortcomings of the prior art hypodermic needle 10.
Figure 1B:
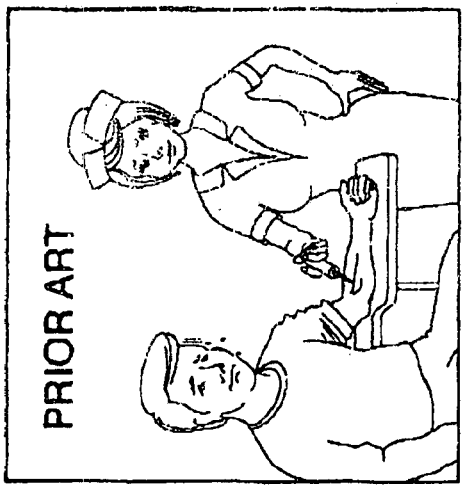
Figure 1C:
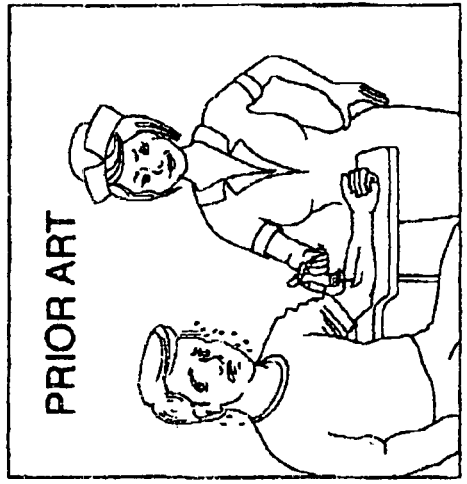
Figure 2A:
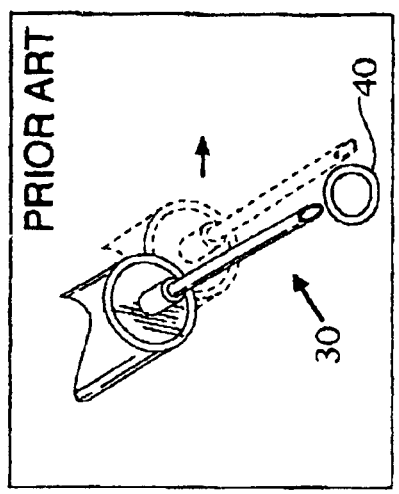
Figure 2B:
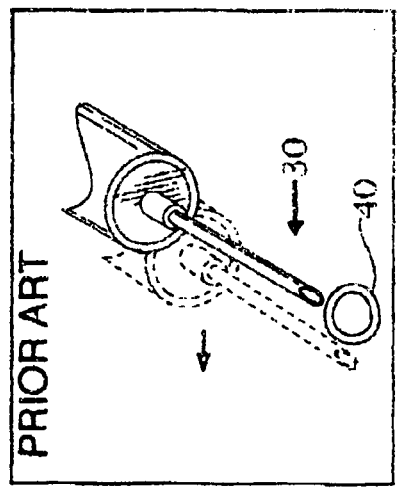
Figure 2C:
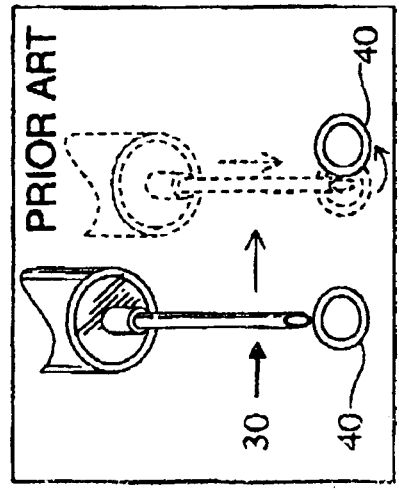

With reference to FIGS. 1A to 2C, injection employing a hypodermic needle of the prior art 30 is shown. Note that in FIGS. 1A and 2A the needle misses the blood vessel 40 and the needle 30 moves to the right or in FIGS. 1B and 2B the needle moves to the left of the blood vessel. In FIGS. 1C and 2C the needle misses its mark (i.e., the vein) because the vein rolls and the needle is unable to meet and penetrate the vein. It is clear as shown by FIGS. 1A–2C that the prior art needle 30 used for injection can be inefficient.

Figure 3:
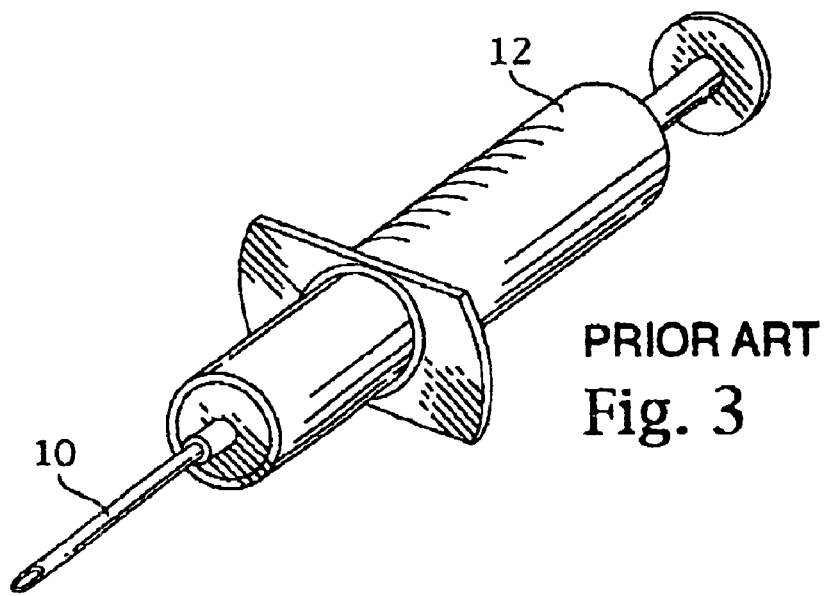
FIG. 3 is a perspective view of a prior art conventional needle 10 attached to a syringe 12.

With reference to FIG. 3, there is shown a perspective view of a prior art single point hypodermic needle 10 attached to a syringe 12.

Turning to FIG. 3, described in greater detail, there is depicted on a somewhat enlarged scale a conventional medical needle adapted for intravenous (I. V.) or similar usage and designated by reference numeral 10. Needle 10 consists of a generally cylindrical tube, typically formed of surgical steel or other suitable material, a first end adapted for connection to, but not limited to, a syringe or flexible tubing, and a second pointed end adapted for penetration through a patient's skin and into a selected bodily cavity, e.g., a blood vessel.

Figure 4:
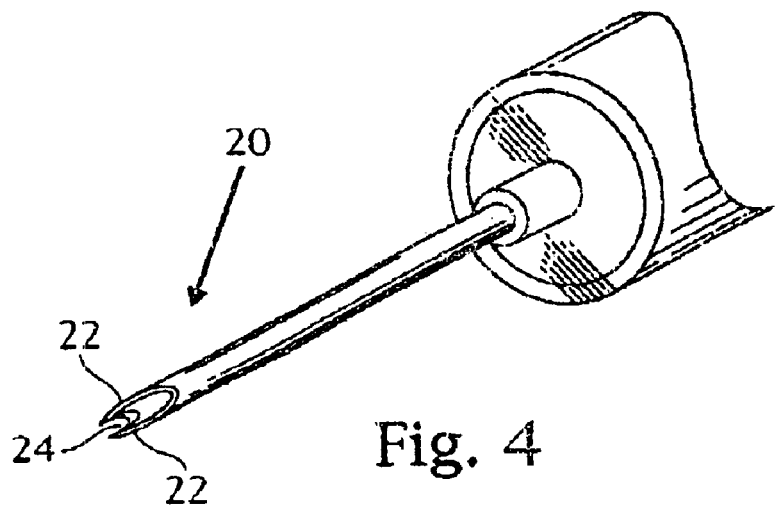
FIG. 4 is a perspective view of the two-pronged hypodermic needle 20 of this invention.

FIG. 4 is a perspective view of the hypodermic needle of this invention 20. The needle 20 has two prongs 22 and a beveled edge 24 between the prongs 22.

With regard to FIGS. 5A to 6D, there is shown detailed comparisons between the needle 30 of Gordon (U.S. Pat. No. 5,064,411) and the hypodermic needle 20 of the disclosed invention.

In regard to FIGS. 5A–5D, there is illustrated the prior art Gordon needle 30. While this needle 30 has a bifurcated tip or double pronged tip 32, the area at the point 34 where the tips 32 are joined is blunt 34 (as best shown by 5C and 5D). This blunt portion of the tip 34 of the needle 30 serves to prevent the needle from penetrating fabric and is a safety feature which shields against in advertent skin puncture. On the other hand with reference to FIGS. 6A–6D, there is described the tip of the hypodermic needle of this invention 20 which has a double-pronged tip 22, but note that between these tips 22 is a beveled edge, i.e., a knife-like edge 24. This configuration allows for the easy penetration of the vein by the needle.

Note carefully, turning to FIGS. 6A–6C and FIG. 7 that the point of the needle 20 is tapered 28 on a tangent to create a sharp point and the prongs 22 are then created by grinding or other suitable means as will be described in FIGS. 13 and 14.

With reference to FIGS. 6A–6D, a medical needle of this invention 20 can be formed of surgical steel and comprises an elongated, generally cylindrical tube having a central axis a first end adapted for connection to diverse medical equipment including, inter alia, a syringe or flexible tubing, and a pointed end adapted for penetration through a patient's skin and into a selected blood vessel.

Figure 7:
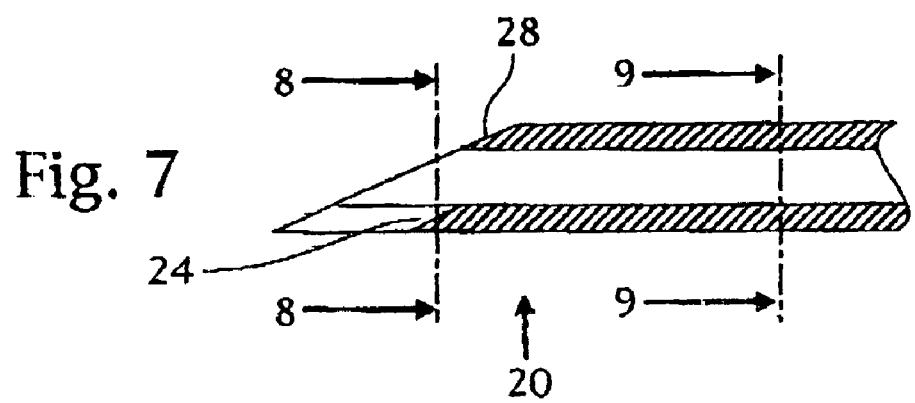
FIG. 7 is a cross-sectional view of the needle of this invention 20 taken along 7—7 of FIG. 6B.
Figure 8:
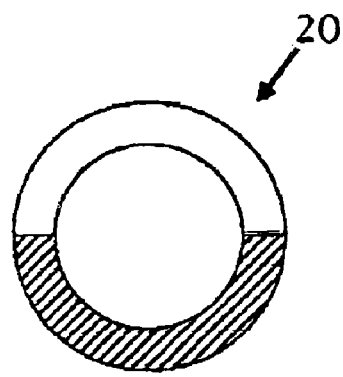
FIG. 8 is a cross-sectional view of the needle of this invention 20 taken along 8—8 of FIG. 7.
Figure 9:
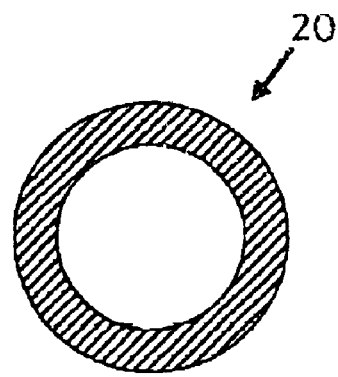
FIG. 9 is a cross-sectional view of the needle of this invention 20 taken along 9—9 of FIG. 7.
Figure 10A:
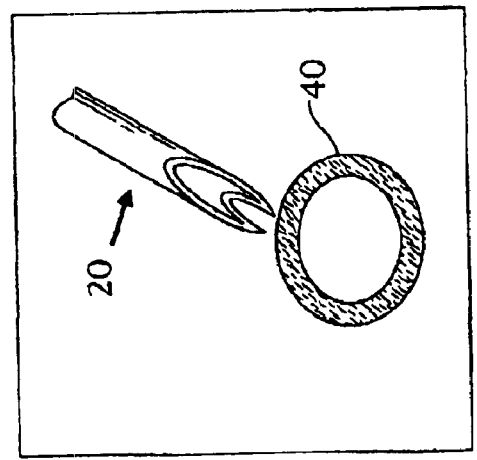
FIGS. 10A–12B are views depicting the effective use of the double-pointed needle of the herein disclosed invention.
Figure 11A:
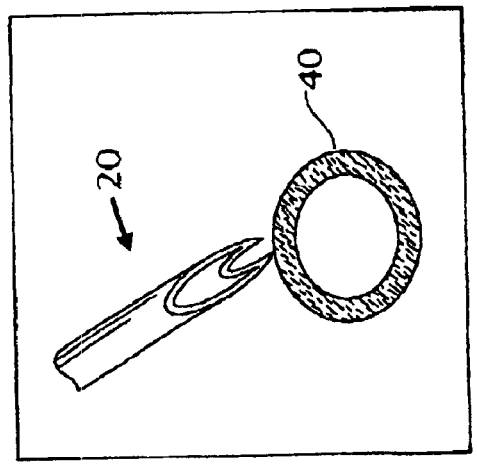

FIGS. 7–9 are sectional views of the hypodermic dermic needle of the disclosed invention 20 and are designed to show the beveled edge 24 between the prongs of the needle.

Figure 12A:
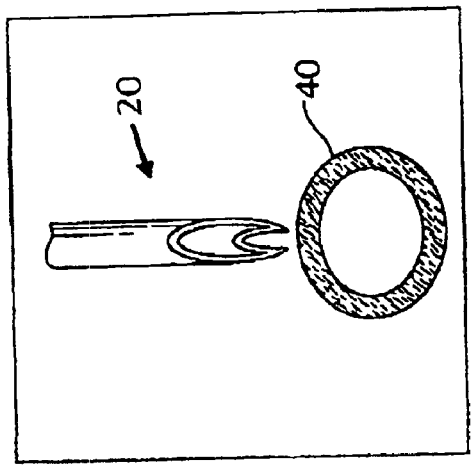
Figure 10B:
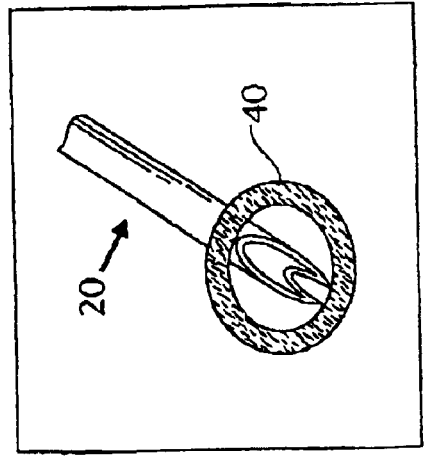
Figure 11B:
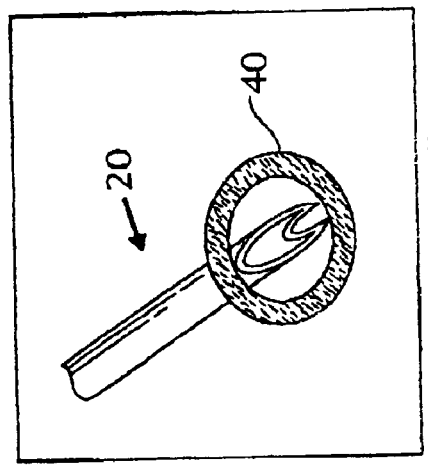
Figure 12B:
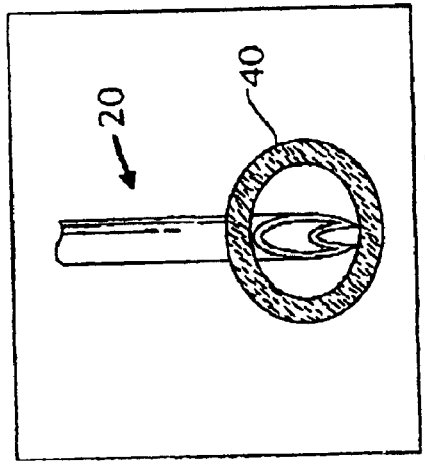

FIGS. 10A–12B depict the fact that the hypodermic needle of this invention 20 can efficiently penetrate a vein 40 when the vein is approached from the right (FIGS. 10A–10B); when approached from the left (FIGS. 11A–11B); or when directly approached (FIGS. 12A–12B). The double-pronged tip of the needle of this invention 20 can straddle a vein to keep it from rolling and thereby allow for efficient penetration of a vein without the need for multiple efforts to penetrate the vein.

Figure 14:
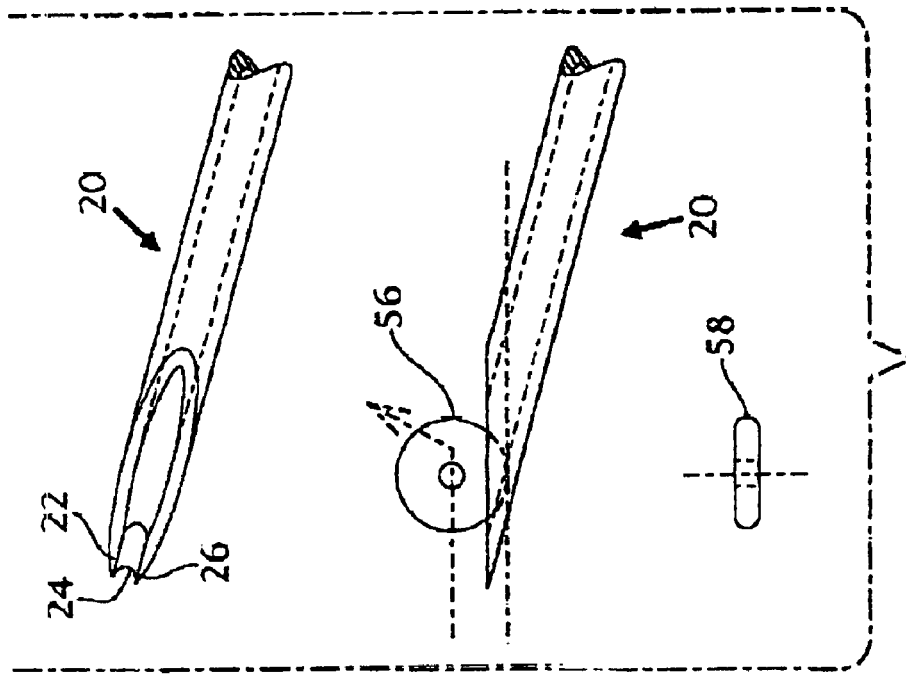
FIGS. 13 and 14 are views illustrating the grinding wheel and angle for grinding the prongs of the hypodermic needle of this invention 20.
Figure 13:
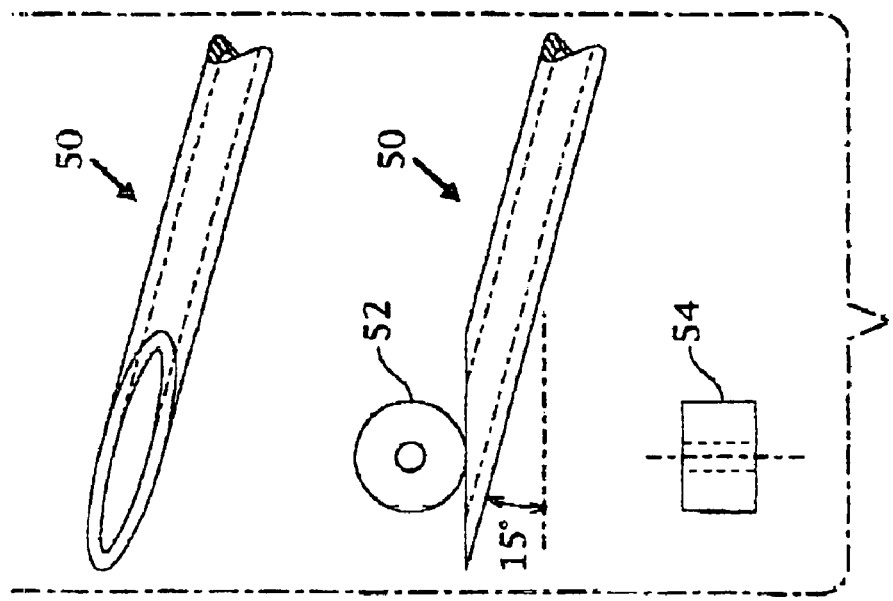

With regard to FIGS. 13 and 14, there are shown the method for forming a double-tipped needle of the prior art and the double-tipped needle of this invention. Note that in FIG. 13, the side view of the wheel 52 and the top view 54 are shown and such a wheel makes the first cut to form a point at the end of the needle 50 and with reference to FIG. 14, the wheel side-view 56 and top view 58 of the wheel which forms prongs 22 and beveled edge 24 are illustrated to form a needle 20 of the disclosed invention.

As seen in FIG. 13, the needle is retained at an angle a of approximately 15° relative to horizontal while a rotatable grinding wheel 52 is translated in a right to left direction thereby forming the pointed end which slopes relative to the central axis at an angle. Any suitable clamping means may be used to firmly hold the needle while the pointed end is ground therein. Alternatively, the grinding wheel may be non-translatable and the needle supported in translatable gripping means whereby the needle can be translated in an opposite direction into the grinding surface of the wheel so as to form pointed end.

With reference to FIG. 13, it can be appreciated since the grinding surface of wheel is cylindrical, the pointed end is established by a plane intersecting central axis at an angle forming the tip of the pointed end a single sharpened prong; and with reference to FIG. 14, wheel 58 has a convex edge grinding surface which forms the prongs and beveled edge between the prongs of the inventive needle. It is also contemplated that pointed end can be formed by a laser or other suitable metal cutting devices.

The initial phases of formation of the pointed end of the needle are substantially the same as those described herein above with regard to conventional needle. That is to say, the tube is ground, laser cut or otherwise machined to produce pointed end. However, in addition to cutting the gently sloping generally planar surface of the pointed end, the tip of pointed end is cut a second time, by suitable means.

An effective means for notching the tip of the pointed end of needle 20 is a rotating grinding wheel having a convex grinding surface which can be translated through pointed end. Alternatively, needle can be translated if wheel is non-translatable. Still further, notching of the pointed end can be performed by laser or other suitable metal cutting means capable of forming a finely machined notch in tube.

Figure 15:
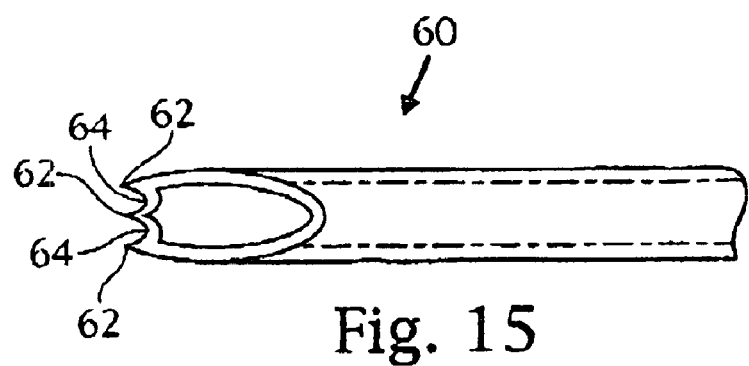
FIG. 15 is a top plan view of a triple-pronged needle.
Figure 5A:
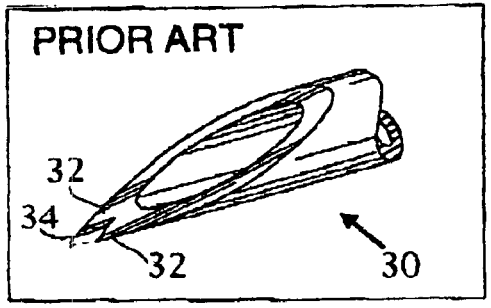
Figure 6A:
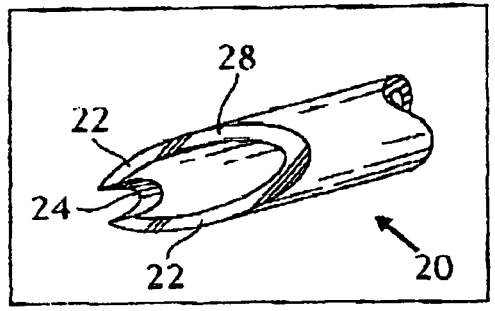
Figure 5B:
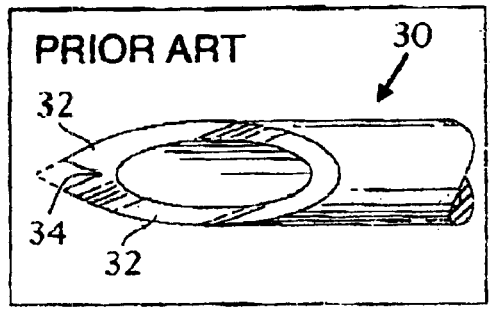
Figure 6B:
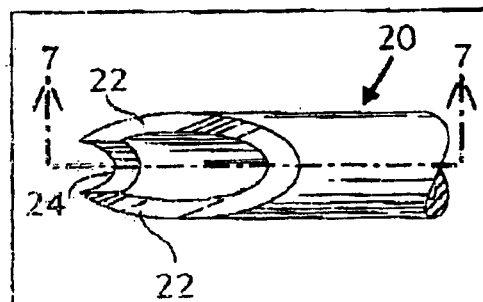
Figure 5C:
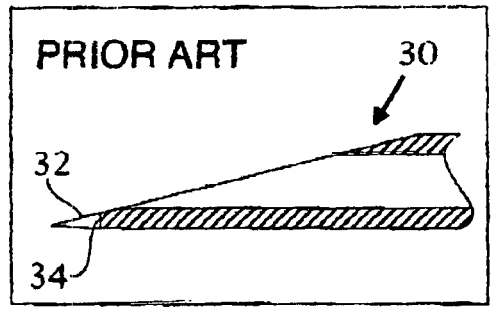
Figure 6C:
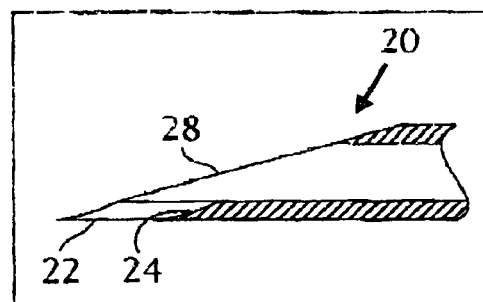
Figure 5D:
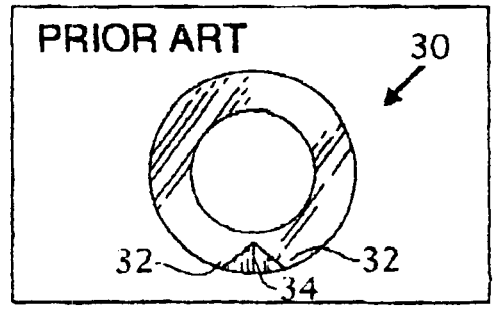
Figure 6D:
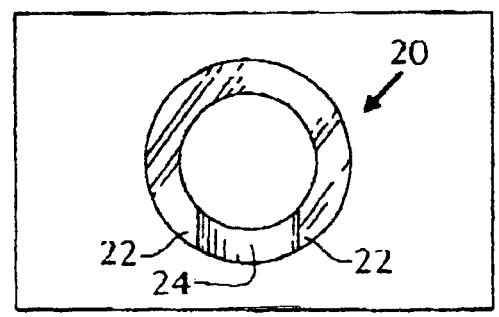

FIG. 15 depicts a further embodiment, herein designated by reference numeral 60, of the medical needle of the present invention wherein three sharpened prongs 62 are provided at the tip of pointed end. This particular construction may be formed by substantially the same process as those described for forming needle except that a grinding wheel having a pair of parallel convex surfaces or other double notching means must be employed to provide the twin notches or beveled edge 64 separating the prongs. Moreover, the relative widths, depths and lengths of the notches in a multiple prong construction as well as their positions relative to central axis may vary according to specified application requirements for the needle. As should by now be appreciated, according to the present invention, any desired number of notches can be provided in the pointed end of a medical needle so long as a plurality of prongs are produced which will capture and deeply penetrate rather than merely displace or lightly prick a blood vessel that may be contacted thereby. As a consequence, satisfactory fluid flow to or from the blood vessel (or other bodily cavity) through the needle may be normally achieved by a single insertion into the skin of a patient of needle or any similar multiple prong needle falling within the scope of the present invention.

The advantages realized by a needle having a plurality rather than a single tissue penetrating prong is that the likelihood of encountering and penetrating the desired blood vessel is increased by a factor substantially corresponding to that of the number of additional prongs 22 and also that, once captured between the prongs 22, the wall of the blood vessel 40 will assuredly be penetrated and not merely displaced by the contact of the needle.

As the reader will appreciate, the medical needle of the present invention finds a variety of beneficial applications. For example, it may be used effectively as a syringe needle, a catheter needle through which a conventional needle may be inserted to introduce and/or withdraw fluid from a bodily cavity, a blood or blood products donation needle, or still other applications requiring a fluid-conducting, bodily cavity penetrable needle. However, the main distinguishing feature of the needle of this invention is that the tip of the needle has two or more prongs having therebetween a beveled configuration and a sharp edge between the prongs which facilitates easy entry of the needle into a blood vessel or like structure.

Although the invention has been described in detail for the purpose of illustration, it is to be understood that such detail is solely for that purpose and that variations can be made therein by those skilled in the art without departing from the spirit and scope of the invention except as it may be limited by the claims.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A medical needle adapted for conducting fluid, said needle comprising:

a generally cylindrical tube having a central longitudinal axis, a first end and a second pointed end adapted for penetration into a body cavity of a subject; and two sharp pointed prongs provided in said pointed end, wherein between said prongs there is a notch having a beveled edge for facilitating the entry of the pointed end of the needle into a body cavity with said prongs being spaced apart substantially less than 180 degrees along the circumference.

2. The medical needle of claim 1 wherein said two sharp pointed prongs are of equal length and parallel to each other.

3. The medical needle of claim 1 wherein said pointed end slopes at a first angle relative to said central axis and said at least one notch slopes at a second angle relative to said first angle.

4. The medical needle of claim 1 wherein said needle is formed of surgical steel.

5. The medical needle of claim 1 wherein the needle is attached to a syringe.

* * * * *